US009358085B2

(12) United States Patent
Doll et al.

(10) Patent No.: US 9,358,085 B2
(45) Date of Patent: Jun. 7, 2016

(54) DEVICE AND METHOD FOR CLEANING DENTAL APPLIANCES

(71) Applicant: The Procter & Gamble Company, Cincinnati, OH (US)

(72) Inventors: Alexander F. Doll, Kronberg (DE); Mario Elmen Tremblay, West Chester, OH (US); Alan David Willey, Cincinnati, OH (US); Luisa Navarro Cerda, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 72 days.

(21) Appl. No.: 14/248,564

(22) Filed: Apr. 9, 2014

(65) Prior Publication Data

US 2014/0311527 A1  Oct. 23, 2014

Related U.S. Application Data

(60) Provisional application No. 61/813,711, filed on Apr. 19, 2013.

(51) Int. Cl.
| | |
|---|---|
| *B08B 7/04* | (2006.01) |
| *A61C 17/00* | (2006.01) |
| *C25B 1/26* | (2006.01) |
| *A45D 44/20* | (2006.01) |
| *A61L 2/18* | (2006.01) |
| *C25B 15/00* | (2006.01) |
| *A46D 1/00* | (2006.01) |
| *A61L 2/20* | (2006.01) |
| *B08B 3/00* | (2006.01) |
| *B08B 3/04* | (2006.01) |
| *B08B 9/00* | (2006.01) |
| *B08B 9/02* | (2006.01) |
| *B08B 9/027* | (2006.01) |

(52) U.S. Cl.
CPC .............. *A61C 17/036* (2013.01); *A45D 44/20* (2013.01); *A46D 1/0207* (2013.01); *A61L 2/18* (2013.01); *A61L 2/20* (2013.01); *C25B 1/26* (2013.01); *C25B 15/00* (2013.01); *A61L 2202/11* (2013.01); *B08B 3/00* (2013.01); *B08B 3/04* (2013.01); *B08B 9/00* (2013.01); *B08B 9/02* (2013.01); *B08B 9/027* (2013.01)

(58) Field of Classification Search
CPC .............. B08B 3/00; B08B 3/04; B08B 9/00; B08B 9/02; B08B 9/027
See application file for complete search history.

(56) References Cited

U.S. PATENT DOCUMENTS

| | | | |
|---|---|---|---|
| 1,845,315 A | 2/1932 | Meikle | |
| 2,236,462 A | 3/1941 | Brinkley | |
| 3,149,358 A | 9/1964 | Chadbourne | |
| 4,710,233 A * | 12/1987 | Hohmann | ............... A61L 2/035 134/1 |
| 4,839,004 A * | 6/1989 | Castellini | ............... A01N 59/08 204/229.2 |
| 4,984,323 A | 1/1991 | Digby | |
| 6,106,691 A * | 8/2000 | Nakamura | ............. A61B 19/34 134/26 |
| 6,117,285 A * | 9/2000 | Welch | .................. A61L 2/0011 204/237 |
| 7,048,842 B2 | 5/2006 | Tremblay et al. | |

(Continued)

*Primary Examiner* — Bibi Carrillo
(74) *Attorney, Agent, or Firm* — Alexandra S. Anoff

(57) ABSTRACT

A device for cleaning a dental appliance is disclosed. The device includes a holding container including an upper portion and a lower portion, the holding container adapted to receive at least one dental appliance; an electrolytic cell for generating chlorine dioxide from a chlorine dioxide precursor; and an electrical current supply including a circuit operably connecting the electrical current supply to the electrolytic cell.

5 Claims, 7 Drawing Sheets

(56) References Cited

U.S. PATENT DOCUMENTS

| | | | |
|---|---|---|---|
| 2004/0037737 A1* | 2/2004 | Marais | A61L 2/035 422/28 |
| 2004/0213698 A1* | 10/2004 | Tennakoon | A61K 8/20 422/37 |
| 2006/0157343 A1* | 7/2006 | Herrington | A61L 2/035 204/232 |
| 2009/0042756 A1 | 2/2009 | Muzik et al. | |
| 2010/0198136 A1 | 8/2010 | Speronello et al. | |
| 2010/0260648 A1 | 10/2010 | Lin | |
| 2014/0311527 A1* | 10/2014 | Doll | A61C 17/036 134/18 |

\* cited by examiner

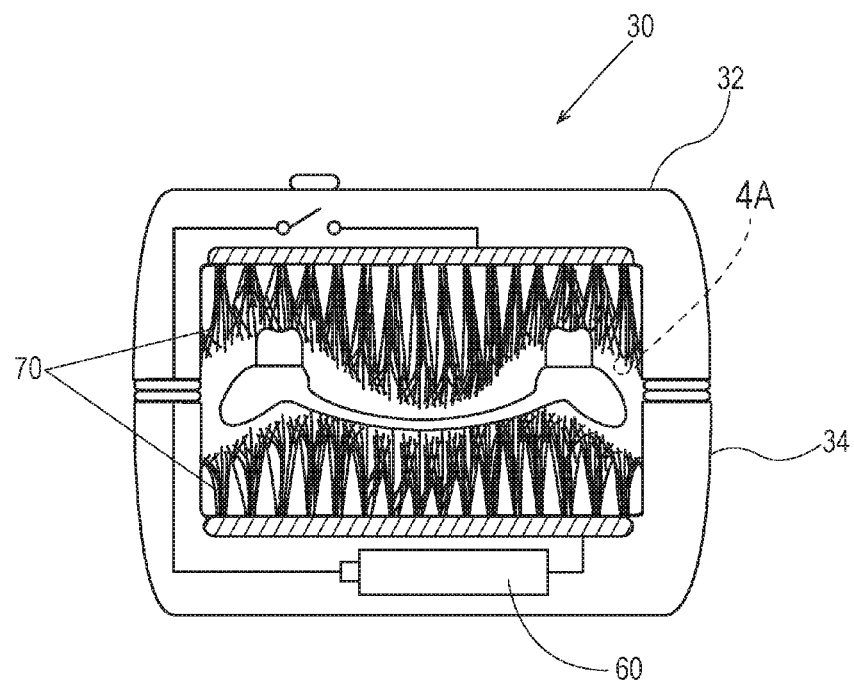
Fig. 4
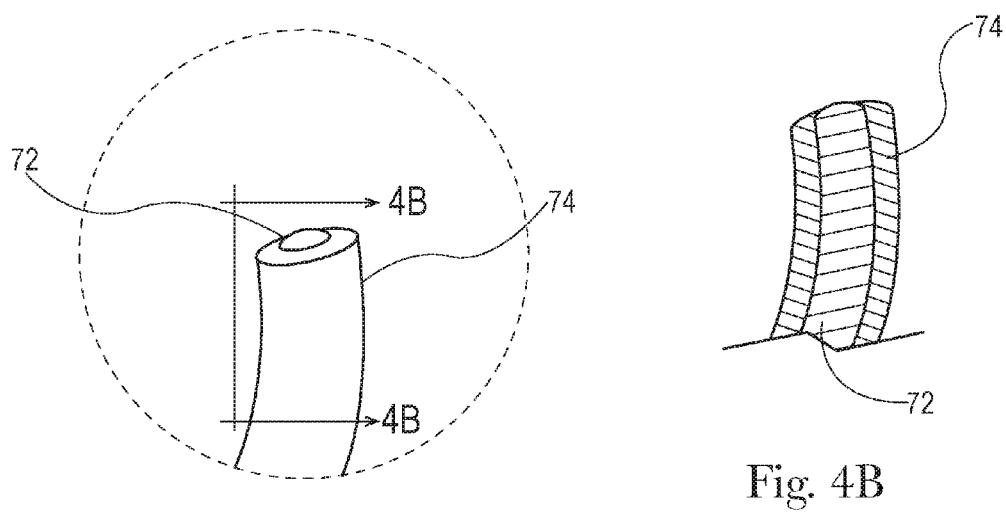
Fig. 4A
Fig. 4B

DEVICE AND METHOD FOR CLEANING DENTAL APPLIANCES

FIELD OF THE INVENTION

The present disclosure relates generally to a device for cleaning dental appliances, and more particularly to a device for cleaning dental appliances that uses chlorine dioxide gas to disinfect the dental appliance.

BACKGROUND OF THE INVENTION

The accumulation of residues on dental appliances (for example, full or partial plate dentures, removable braces, retainers, mouth guards, snoring devices, etc.) is a familiar and persistent problem for wearers of such appliances. These residues often consist of some combination of food particles and biofilm (i.e., plaque), the latter of which is a complex aggregate of oral bacteria, fungi and other organisms; this plaque is estimated to contain more than 100,000,000,000 organisms per milligram and involve more than 30 species. Many of these bacteria produce volatile sulfur compounds as waste products. If the dental appliance is not rid of food particles and biofilm on a regular basis, the malodourous waste products will accumulate, causing the wearer to exhibit bad breath. Even more serious is the potential for pathogenic bacteria to inhabit the biofilm, increasing the likelihood of infection for the wearer. Over time, the biofilm will be converted into dental calculus, which consists of inorganic mineralized salts derived from saliva, bacteria, and food particles, as described in U.S. Pat. No. 6,670,312 B2.

In addition to accumulation of residues on the appliance, staining is another widespread problem reported by wearers of dental appliances. Staining of dental appliances is particularly pronounced among coffee and tea drinkers, smokers, and those who use chewing tobacco. Stained dental appliances are unsightly and can be a source of embarrassment for the appliance wearer.

Although many wearers choose to brush their dental appliance with toothpaste (i.e., mechanical cleaning), others find it more convenient to soak their appliance in a cleansing solution. Some wearers do both, brush their dental appliance with toothpaste and soak in a cleansing solution. This cleansing solution is often generated by mixing a commercially available cleansing tablet or powder with water. Though such compositions have achieved considerable popularity and commercial success, there is a continuing need for improvement, especially with respect to plaque removal.

Chlorine dioxide is known to be a disinfectant, as well as a strong oxidizing agent. The bactericidal, algaecidal, fungicidal, bleaching and deodorizing properties of chlorine dioxide are also well known. However, chlorine dioxide is a troublesome material to transport and handle at high aqueous concentrations, due to its low stability and high corrosivity.

Accordingly, there is a need for simple, safe and convenient devices, systems and methods that are effective for disinfecting, cleaning, deodorizing, bleaching and removing plaque and other residues from a wide variety of dental appliances by the use of chlorine dioxide generated in situ.

SUMMARY OF THE INVENTION

In one embodiment, a device for cleaning a dental appliance is provided. The device includes a holding container including an upper portion and a lower portion, the holding container adapted to receive at least one dental appliance; an electrolytic cell for generating chlorine dioxide from a chlorine dioxide precursor; and an electrical current supply including a circuit operably connecting the electrical current supply to the electrolytic cell.

In another embodiment, a pre-packaged arrangement is provided. The pre-packaged arrangement includes a cleaning composition including a chlorite source; and a device for cleaning a dental appliance, the device including a holding container including an upper portion and a lower portion, the holding container adapted to receive at least one dental appliance; an electrolytic cell for generating chlorine dioxide; and an electrical current supply including a circuit operably connecting the electrical current supply to the electrolytic cell. The cleaning composition and the device for cleaning a dental appliance are arranged relative to each other for distribution together as a single unit.

In another embodiment, a method of cleaning a dental appliance outside of the oral cavity is provided. The method includes the steps of: providing a device for cleaning a dental appliance, the device including a holding container including an upper portion and a lower portion, the upper portion adapted to receive at least one dental appliance; and an electrolytic cell for generating chlorine dioxide from a chlorine dioxide precursor; placing the dental appliance in the upper portion of the holding container; providing a cleaning composition including a chlorine dioxide precursor; electrolyzing the cleaning composition thereby forming an aqueous solution including chlorine dioxide; and maintaining the dental appliance in contact with the chlorine dioxide solution for at least about 30 seconds.

These and other features, aspects and advantages of specific embodiments will become evident to those skilled in the art from a reading of the present disclosure.

BRIEF DESCRIPTION OF THE DRAWINGS

While the specification concludes with claims which particularly point out and distinctly claim the subject matter that is regarded as the invention, it is believed the various embodiments will be better understood from the following description taken in conjunction with the accompanying drawings, in which:

FIGS. 2A and 2B are cut-away views of the cleaning device shown in FIG. 2;

FIG. 4 is a cut-away view of one embodiment of a cleaning device and conductive bristles according to one or more embodiments illustrated and described herein;

FIG. 4A is an exploded view of a conductive bristle shown in FIG. 4;

FIG. 4B is a cross-sectional view of the conductive bristle taken along line 4B of FIG. 4A;

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

The terms "clean", "cleansing" or "cleaning" are used interchangeably herein to refer to removing food particles, stain and other oral debris, both on the surface and within the pores of a dental appliance, with the formulation disclosed herein.

The embodiments described below use dentures as an example of a dental appliance that can be cleaned in accordance with the present disclosure. However, the cleaning device as described herein also applies to additional dental appliances such as partial dentures, artificial teeth, removable orthodontic bridges and denture plates, both upper and lower types, removable braces, retainers, mouth guards, snoring devices, night guards to prevent bruxism and/or Temporomandibular joint (TMJ) disorder, and the like.

Dental Appliance Cleaning Device

The present disclosure employs a device for cleaning dental appliances having an electrical current passing through cleaning solution between an anode and a cathode to convert a chlorite salt precursor dissolved within the solution into chlorine dioxide. More specifically, chlorine dioxide is generated from a halogen dioxide salt, for example, chlorite salts. The electrochemical generation of chlorine dioxide from aqueous sodium chlorite is represented in the reaction:

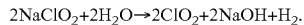

$$2NaClO_2 + 2H_2O \rightarrow 2ClO_2 + 2NaOH + H_2.$$

In another embodiment, hypobromite ($BrO^-$) generated from sodium bromide may be used to provide antibacterial efficacy and bleaching.

Figure 1:
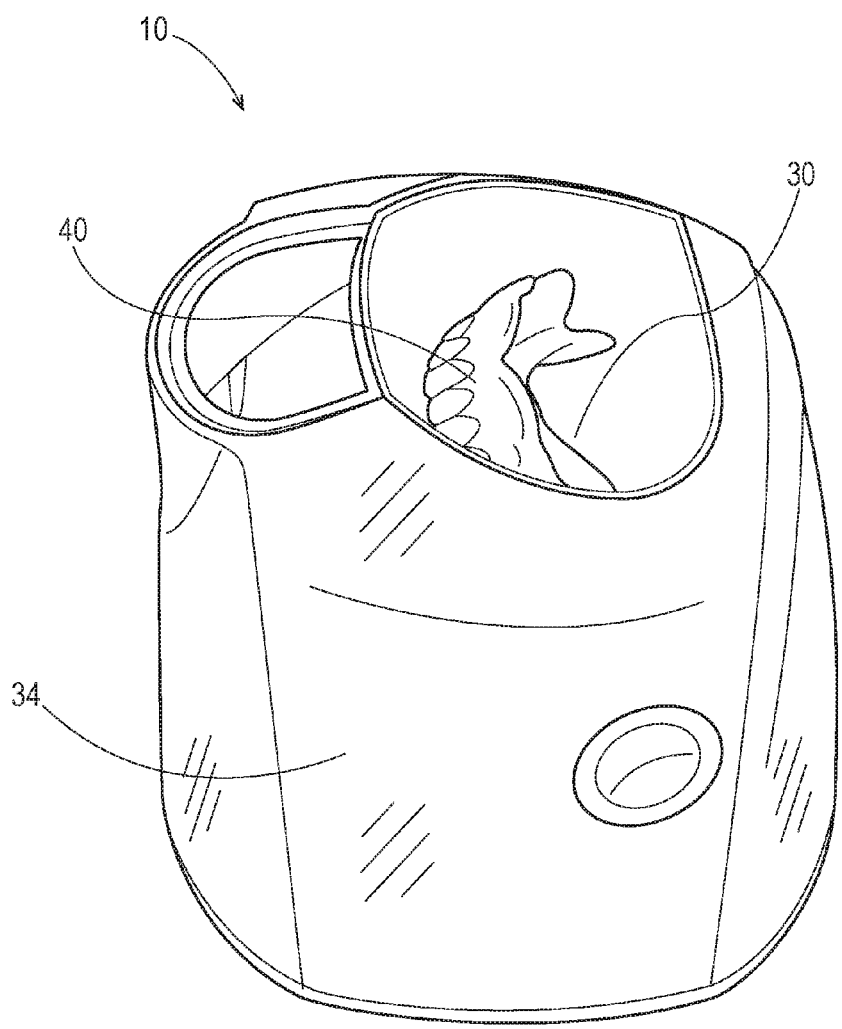
FIG. 1 is an assembled perspective view of one embodiment of a cleaning device according to one or more embodiments illustrated and described herein.
Figure 2:
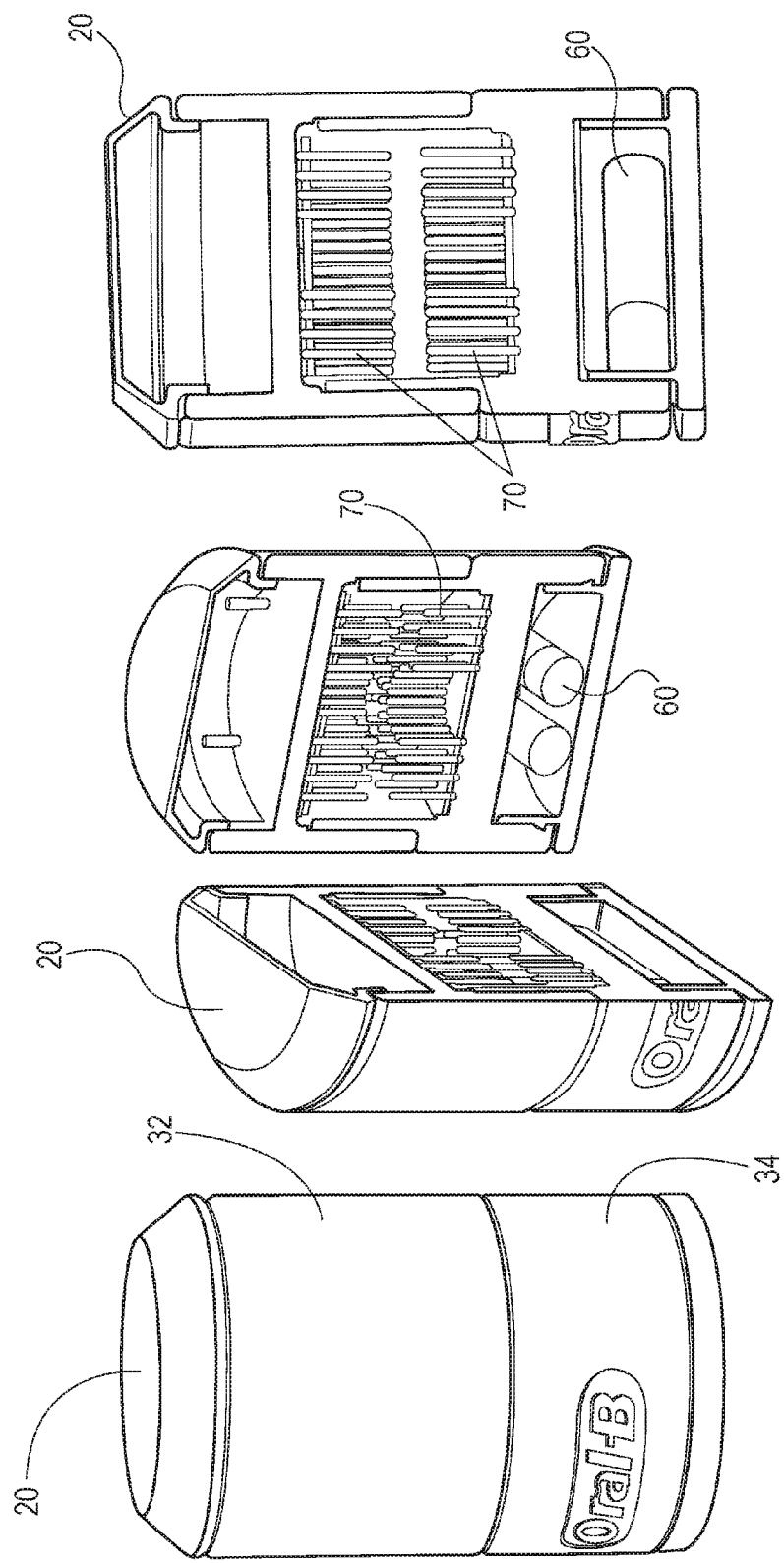
FIG. 2 is a perspective view of one embodiment of a cleaning device according to one or more embodiments illustrated and described herein.

Referring now to FIG. 1, one embodiment of a cleaning device 10 for dental appliances is illustrated. As further shown in FIGS. 2, 2A and 2B, device 10 includes an upper cover 20, a holding container 30 for holding at least one dental appliance 40, an electrolytic cell 50, and a power source 60.

In one embodiment, the upper cover 20 may be in the form of a plate or disk and removably positioned on an upper portion of the device. In one example, the upper cover 20 may be pin connected to the holding container 30 or may be hinge connected to the upper portion of the device, whereby it may releasably engage a lug or spring latch in order to prevent accidental opening. Any other known attachment means for attaching a cover to a container may also be used.

Figure 3:
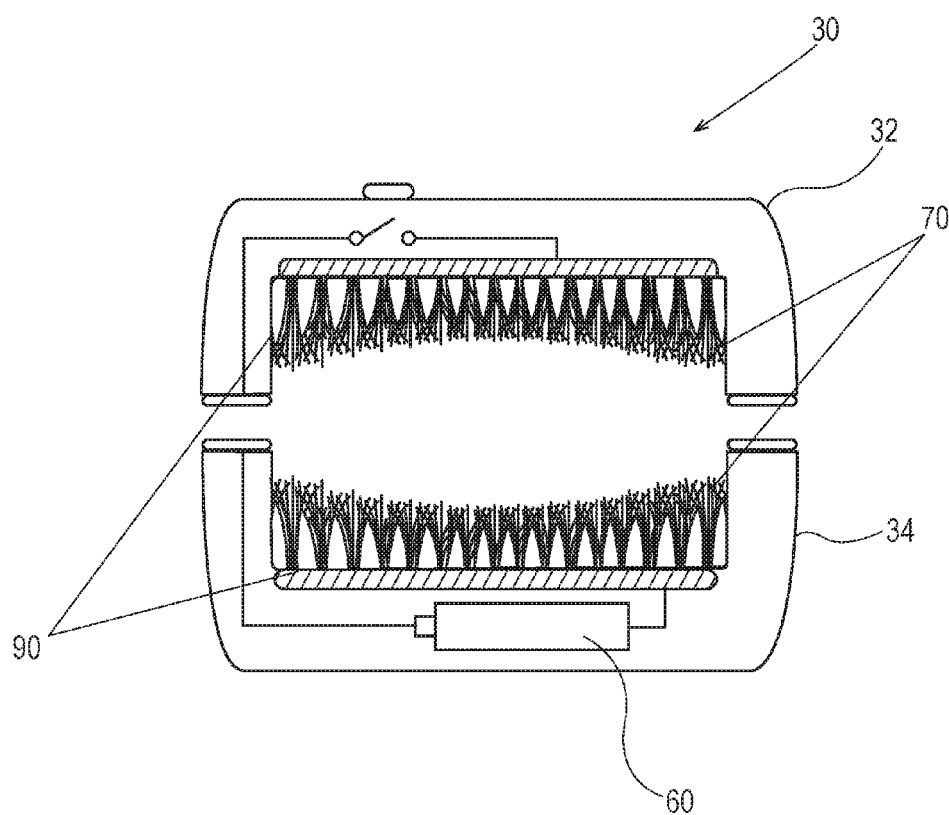
FIG. 3 is a cut-away view of one embodiment of a cleaning device according to one or more embodiments illustrated and described herein.
Figure 5:
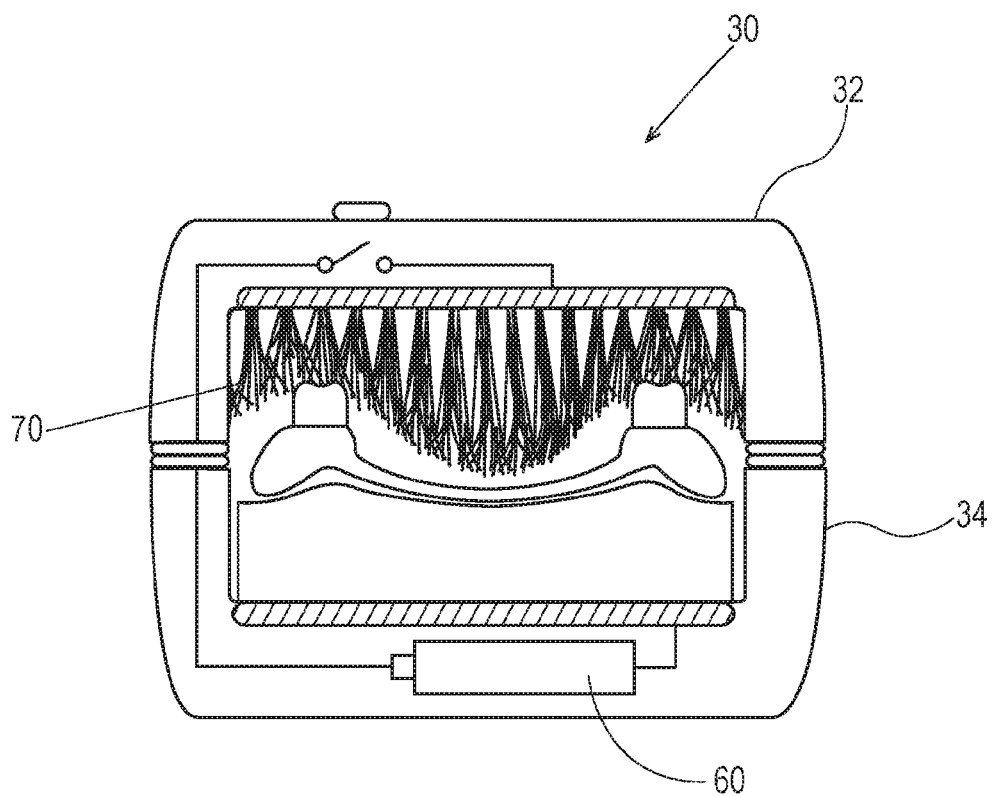
FIG. 5 is a cut-away view of one embodiment of a cleaning device and conductive bristles according to one or more embodiments illustrated and described herein.

In one embodiment as shown in FIG. 3, the holding container 30 includes an upper portion 32 and a lower portion 34. In operation, a wearer would open the device and place a dental appliance 40 into the holding container 30 for cleaning such that the dental appliance is supported by the lower portion 34 as shown in FIG. 4. In some embodiments, a plurality of cleaning elements 70 are provided in opposed relation on the upper portion 32 and the lower portion 34. In another embodiment as shown in FIG. 5, a plurality of cleaning elements 70 may only be provided on one of the upper or lower portions. In one embodiment, at least one of the upper portion 32 and the lower portion 34 of the holding container is movable. In one embodiment, at least one of the upper portion 32 and the lower portion 34 of the holding container is rotatable relative to the other portion.

Any suitable method of mounting the cleaning elements 70 to the upper or lower portion may be used. For example, where the cleaning elements 70 comprise a plurality of bristles, methods such as hot tufting, gluing, stapling, and the like, may be utilized. As another example, where the cleaning elements 70 comprise a plurality of elastomeric elements, methods such as gluing, snap-fitting, welding, molding, etc. may be utilized.

The term "cleaning elements" is used to refer to any suitable element for engaging a dental appliance for purposed of cleaning. Some suitable elements include bristle tufts, elastomeric massage elements, elastomeric cleaning elements, massage elements, tongue cleaners, soft tissue cleaners, hard surface cleaners, combinations thereof, and the like. The cleaning elements 70 may include a wide variety of materials and may have a number of different configurations. Any suitable material and/or any suitable configuration may be utilized. For example, in some embodiments, the cleaning elements 70 may comprise tufts. The tufts may comprise a plurality of individual filaments which are securely attached to a cleaning element support member. Such filaments may be polymeric and may include polyamide or polyester or a thermoplastic elastomeric polyamide grind or mixtures thereof. The longitudinal and cross sectional dimensions of the filaments and the profile of the filament ends can vary. Additionally, the stiffness, resiliency and shape of the filament end can vary. Some examples of suitable dimensions include a length between about 6.0 mm and about 10 mm and in another embodiment between about 7.0 mm and about 8.5 mm, or any individual number within these ranges. Additionally, the filaments may include a substantially uniform cross-sectional dimension of between about 100 to about 350 microns, in another embodiment in a range of between about 125 microns and about 175 microns, or any individual number within these ranges. The tips of the filaments may be any suitable shape, examples of which include a smooth tip, a rounded tip, tapered and a pointed tip. In some embodiments, the filaments may include a dye which indicates wear of the filaments as described in U.S. Pat. No. 4,802,255. Other suitable examples of filaments are described in U.S. Pat. No. 6,018,840. In some embodiments, the cleaning element fields may comprise fins as described in U.S. Pat. No. 6,553,604, and U.S. Patent Application Publication Nos. 2004/0177462; 2005/0235439; and 2005/0060822. In some embodiments, the cleaning element fields may comprise a combination of fins and tufts.

In one embodiment the cleaning elements 70 may include bristles that are fully conductive or that contain an electrically conductive core so that electricity is in direct contact with the surface of the dental appliance during cleaning. In one embodiment as shown in FIG. 4A, each bristle includes an electrically conductive core 72 having a first electrical resistance and a sheath 74 around the core 72, having a second electrical resistance that is greater than the first electrical resistance. Core 72 of each bristle is electrically connected to an electrical current source via a conductive element. Core 72 can be made from an electrically conductive polymer or from a metallic material. Sheath 74 can be made from any substantially electrically insulating polymer. In one embodiment, the conductive bristles act as electrodes. In one example, the conductive bristles on the top half may be anodic and the conductive bristles on the bottom half may be cathodic. Depending on the positive or negative charge of the bristles, either a basic or acidic pH may be maintained on the surface to be disinfected.

As an example and not a limitation, the electrically conductive bristle 70 may comprise a polymer having electrically conductive particles (e.g., electrically conductive carbon particles, nano-particles, conductive soot) embedded therein. In another embodiment, bristle 70 may be coated with a conductive film or material that loses conductivity over time. For example, the colored film that is applied by a ring dye process to provide a visual indication to the users as to the wear of the bristles may be made electrically conductive.

In another embodiment, the bristle 70 comprises an electrically conductive wire core 72 that is made out of any electrically conductive material, such as a pliable metallic material, and an outer insulator jacket 74 that surrounds the electrically conductive wire core. The outer insulator jacket 74 is made of a non-conductive material that is sufficiently pliable to be used in a tooth brush application. In one embodiment, an exposed portion of the electrically conductive wire core 72 extends beyond the outer insulator jacket 74 such that it is exposed to the oral cavity of the user and may act as the first electrode as described above.

Figure 6:
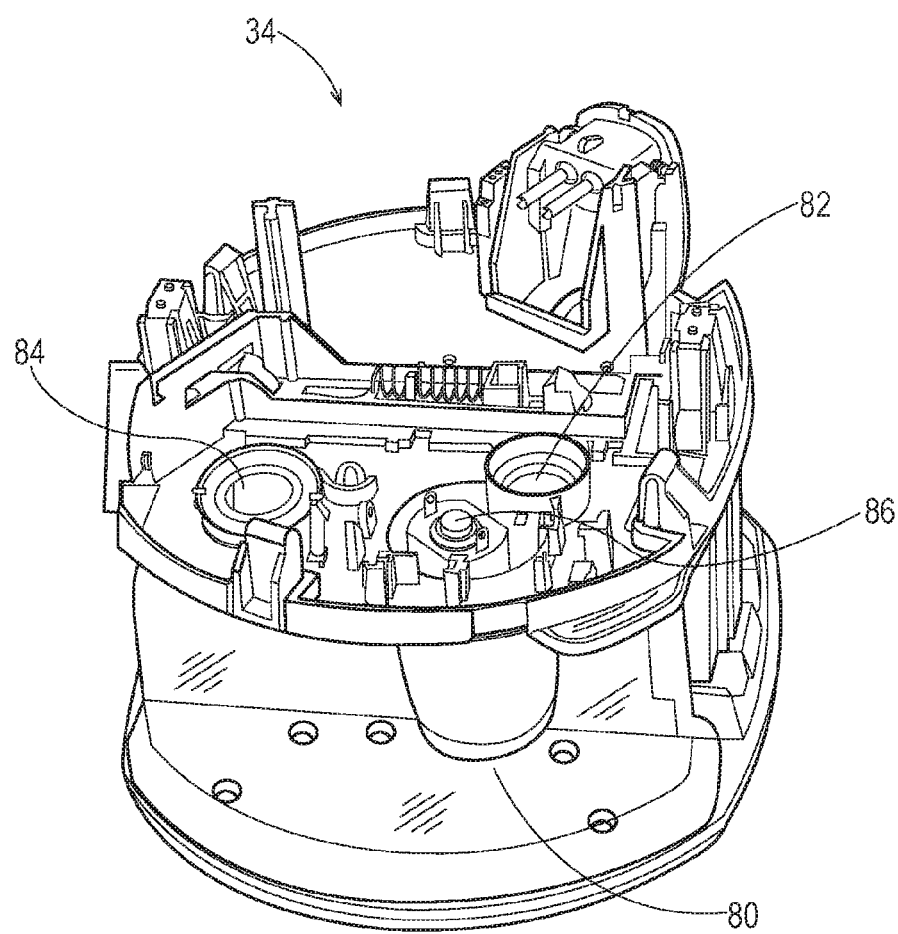
FIG. 6 is a perspective view of one embodiment of the lower portion of the holding container according to one or more embodiments illustrated and described herein.
Figure 7:
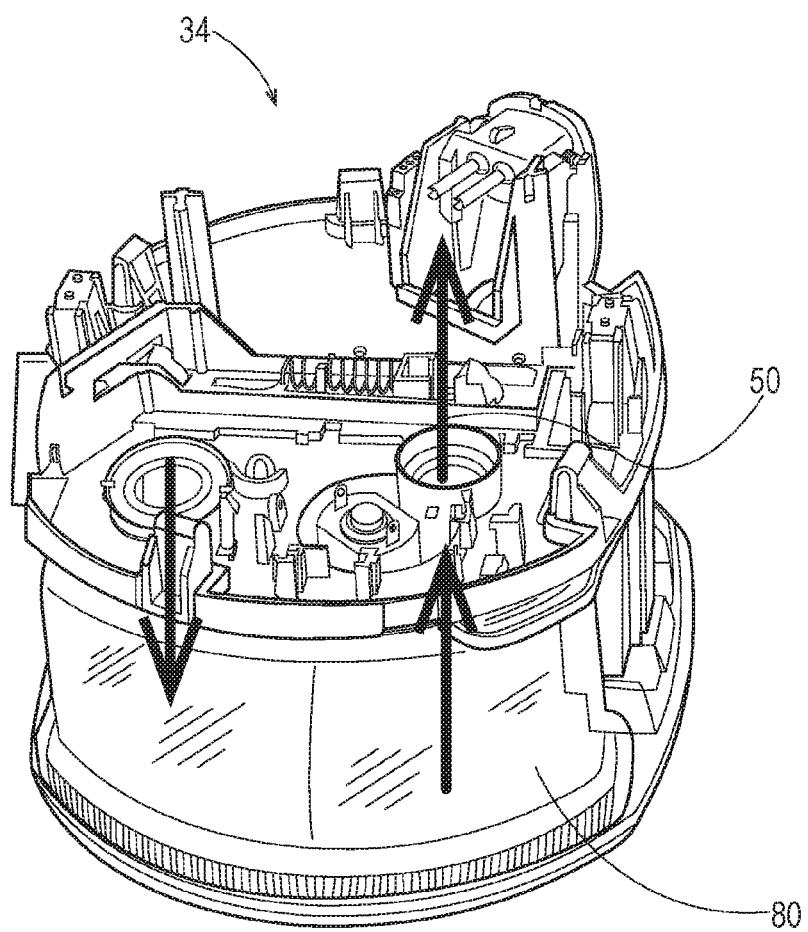
FIG. 7 is a perspective view of one embodiment of the lower portion of the holding container according to one or more embodiments illustrated and described herein.

FIGS. 6 and 7 illustrate the lower portion 34 of device 10. Lower portion 34 may include a fluid container 80 attached to and located beneath the holding container 30. The fluid container 80 is in fluid communication with the holding container. In one embodiment, the fluid container 80 includes the electrolytic cell 50. Fluid container 80 may also include an inlet port 82 and an outlet port 84 for controlling the flow of fluid from the fluid container to the holding container 30 and back again to the fluid container 80, and a circuit board. In another embodiment, a circuit board may also be located in the upper portion 32 of the device. In one embodiment, device 10 also includes a pump 86 in fluid communication with the holding container 30 and the fluid container 80. The pump 86 is connected to the fluid container 80 in order to deliver the cleaning fluid to the holding container 30 via the inlet port 82 during a cleaning cycle. Once the cleaning cycle has been completed, the pump 86 acts to remove the cleaning fluid from the holding container 30 via the outlet port 84. Operation of a switching means, for example, an ON/OFF switch or button caused the pump 86 to be driven which delivers the cleaning fluid to the holding container 30 for a predetermined period of time, for example, in one embodiment at least about 30 seconds; in another embodiment at least about 60 seconds; in another embodiment at least about 90 seconds; and in yet another embodiment at least about 120 seconds. On completion of the cleaning cycle, the pump 86 is automatically turned off.

The fluid container 80 may be provided with a fluid level indicating means enabling the amount of cleaning fluid to be monitored.

Cleaning Fluid

In one embodiment, the cleaning solution may comprise the halogen dioxide salt, sodium chlorite. Sodium chlorite is not a salt ordinarily found in tap water, well water, and other water sources. Consequently, the sodium chlorite salt is added to the cleaning solution at a desired concentration generally of at least about 1100 parts per million (ppm). The term ppm, as used herein, means that one ppm is substantially equivalent to 1 milligram of something per liter of water (mg/l). The desired concentration of the sodium chlorite salt is dependent on the desired decontaminant targeted.

The range of chlorine dioxide conversion that is achievable in the electrolytic cells described herein generally ranges from greater than about 0.01% to less than 100%. The level of conversion is dependent most significantly on the design of the cleaning device 10, as well as on the electrical current properties used in the cleaning device 10.

The cleaning solution comprising the sodium chlorite can be provided in a variety of ways. In one embodiment, a solid form of the sodium chlorite, for example, a powder, pill or tablet, can be mixed into an aqueous solution, for example tap water, by the user to form a dissolved solution. This may be referred to as an open system as the user makes the cleaning solution as part of the cleaning process. In another embodiment, the system may be closed, i.e., the solution is provided as a pre-mixed solution with no mixing by the user. In one embodiment, the solution may be provided in a cartridge that can be loaded into the device prior to cleaning.

In another embodiment, the cleaning solution may comprise one or more other salts in addition to sodium chlorite. These optional salts can be used to enhance the disinfection and bleaching performance of the cleaning solution. For example, an alkali halide such as sodium chloride may be used.

In one embodiment, the pH of the cleaning solution is from about 7 to about 12. The cleaning solution may also contain a variety of miscellaneous additives, including but not limited to therapeutic actives, flavorants, whiteners, chelants, surfactants, pH adjusting agents, buffers, bleach catalysts, rheology modifiers, dye/colorants, and optical brighteners.

Therapeutic actives may be present at a level of from about 1, 5, 10, 15, 20, 25, 30%, to about 3, 5, 10, 15, 20, 30, 50, 70%, or any combination thereof. Therapeutic actives include, for example, antimicrobial and antibacterial agents such as iodine, triclosan, peroxides, sulfonamides, bisbiguanides, or phenolics; antibiotics such as tetracycline, neomycin, kanamycin, metronidazole, cetylpyridinium chloride, domiphen bromide, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; fluorides such as sodium fluoride, stannous fluoride, MFP (monofluorophosphate); anesthetic agents such as lidocaine or benzocaine; whitening agents such as peroxide; anti-fungals such as those for the treatment of candida albicans; insulin; steroids; herbal and other plant derived remedies; and baking soda. Other suitable therapeutic actives are discussed in the Physicians' Desk Reference $62^{nd}$ Ed., 2008 and the Physicians' Desk Reference for non-prescription drugs, dietary supplements, and herbs, $29^{th}$ Ed, (portions pertaining to non-prescription drugs, dietary supplements, and herbs are hereby incorporated by reference.)

According to one embodiment, the active is selected from the group consisting of: anti-calculus, fluoride ion source, stannous ion source, whitening, antimicrobial, anti-plaque, anti-stain, anti-deposition, anti-gingivitis, anti-tartar, anti-periodontitis, anti-sensitivity, anti-cavity, anti-inflammatory, nutrients, antioxidants, anti-viral, anti-fungal, analgesic, anesthetic, H-1 and H-2 antagonists, and combinations thereof.

The cleaning compositions of the present disclosure may also include one or more components which provide flavor, fragrance, and/or sensate benefit (ex. warming or cooling agents). Suitable components include, for example, menthol, wintergreen oil, peppermint oil, spearmint oil, leaf alcohol, clove bud oil, anethole, methyl salicylate, eucalyptol, cassia, 1-8 menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal, their derivatives, and combinations thereof. In one embodiment, the active is an aromatic such as camphor, eucalyptus oil, and aldehyde derivatives such as benzaldehyde; or a combination thereof.

These agents may be present at a level of from about 0% to about 40%, in another embodiment from about 0.05 to about 5%, and in another embodiment from about 0.1 to about 2%, by weight of the composition. Other suitable ingredients include colorants and preservatives (such as methyl and propyl parabens, for example). The colorants and preservatives may be present at levels of from about 0% to about 20%, by weight of the composition, in another embodiment from about 0.1%, 0.2, 1, 2, 5, to about 1, 5, 10, 20%, or any combination thereof.

The cleaning compositions of the present disclosure may also include one or more optical brighteners. Suitable examples include triazine-stilbenes (di-, tetra- or hexa-sulfonated), coumarins, imidazolines, diazoles, triazoles, benzoxazolines and biphenyl-stilbenes.

Electrolytic Cell

The electrolytic cell according to the present disclosure, generates chlorine dioxide from sodium chlorite by flowing electrical current through the cleaning solution that passes through the holding chamber.

In one embodiment, the cleaning device 10 includes an electrolytic cell 50 with at least a pair of electrodes, an anode and a cathode. A suitable example of electrolytic cells for use in device 10 are described in U.S. Pat. No. 7,048,842.

Electrical Current Supply

An electrical current supply provides a flow of electrical current between the electrodes and across the passage of cleaning solution passing across the electrodes. In some embodiments, the electrical current supply is an externally connected power supply unit (such as a transformer) that is either an alternating-current transformer or a direct current transformer. In this example, the wearer would first need to insert a plug of the transformer into a power jack located on the device prior to activating the device.

In other embodiments involving portable or small, personal use systems, such as the disclosed cleaning device, an exemplary electrical current supply is a battery or set of batteries, selected from an alkaline, lithium, silver oxide, manganese oxide, or carbon zinc battery. The batteries can have a nominal voltage potential of 1.5 volts, 3 volts, 4.5 volts, 6 volts, or any other voltage that meets the power requirements of the cleaning device. In one embodiment, common-type batteries such as "AA" size, "AAA" size, "C" size, and "D" size batteries having a voltage potential of 1.5 V are appropriate. It should be appreciated that smaller voltage batteries may be used, if desired. Two or more batteries can be wired in series (to add their voltage potentials) or in parallel (to add their current capacities), or both (to increase both the potential and the current). Re-chargeable batteries and mechanical wound-spring devices can also be employed.

Another alternative is a solar cell that can convert (and store) solar power into electrical power. Solar-powered photovoltaic panels can be used advantageously when the power requirements of the flow-through electrolysis cell 20 draws currents below 2000 milliamps across voltage potentials between 1.5 and 9 volts.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of cleaning a dental appliance outside of an oral cavity, comprising the steps of:
   providing a device for cleaning a dental appliance, the device including a holding container including an upper portion and a lower portion, the upper portion adapted to receive at least one dental appliance; and an electrolytic cell for generating chlorine dioxide from a chlorine dioxide precursor; wherein the device further comprises a plurality of cleaning elements disposed on at least one of the upper portion or the lower portion of the holding container, wherein the plurality of cleaning elements comprises at least one conductive bristle;
   placing the dental appliance in the upper portion of the holding container;
   providing a cleaning composition including a chlorine dioxide precursor;
   electrolyzing the cleaning composition thereby forming an aqueous solution including chlorine dioxide; and
   maintaining the dental appliance in contact with the chlorine dioxide solution for at least about 30 seconds, wherein the at least one conductive bristle is in direct contact with the dental appliance during cleaning.

2. The method of claim 1 wherein the plurality of cleaning elements is disposed on both the upper portion and the lower portion of the holding container in opposed relation.

3. The method of claim 1 wherein at least one of the upper portion or the lower portion of the holding container is movable to clean the dental appliance disposed there between.

4. The method of claim 3 wherein at least one of the upper portion or the lower portion of the holding container is rotatable.

5. The method of claim 1 wherein the at least one conductive bristle includes an electrically conductive material within a polymer.

* * * * *